United States Patent [19]

Cantello et al.

[11] Patent Number: 4,918,091
[45] Date of Patent: Apr. 17, 1990

[54] NOVEL THIAZOLIDINEDIONES

[75] Inventors: Barrie C. C. Cantello; Richard M. Hindley, both of Epsom, England

[73] Assignee: Beecham Group p.l.c., Brentford, United Kingdom

[21] Appl. No.: 206,219

[22] Filed: Jun. 13, 1988

[30] Foreign Application Priority Data

Jun. 13, 1987 [GB] United Kingdom ............... 8713863
Sep. 4, 1987 [GB] United Kingdom ............... 8720824

[51] Int. Cl.$^4$ ............... C07D 277/34; A61K 31/425
[52] U.S. Cl. ............................ 514/369; 548/183
[58] Field of Search .................... 548/183; 514/369

[56] References Cited

U.S. PATENT DOCUMENTS 4,287,200 9/1981 Kawamatsu ..................... 548/183

FOREIGN PATENT DOCUMENTS 0008203 2/1980 European Pat. Off. ............ 548/183
0084926 8/1983 European Pat. Off. ............ 548/183
0177353 4/1986 European Pat. Off. ............ 548/183
0193256 9/1986 European Pat. Off. ............ 548/183
0208420 1/1987 European Pat. Off. ............ 548/183

OTHER PUBLICATIONS

European Search Report–Application No.: EP 88 30 5284.
Chemical and Pharmaceutical Bulletin, vol. 30, No. 10, 1982, pp. 3500–3600.
T. Sohda et al., "Studies on Antidiabetic Agents II, Synthesis of 5-(4-(1-Methylcyclohexylmethoxy)-Benzyl)Thiazolidine-2,4-Dione (ADD-3878) and its Derivatives", pg. 3587, table V, compound no. 80, pg. 3589, lines 10–12.

Primary Examiner—Robert Gerstl
Attorney, Agent, or Firm—Hopgood, Calimafde, Kalil, Blaustein & Judlowe

[57] ABSTRACT

A compound of formula (I):

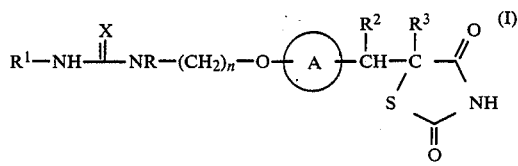

or a tautomeric form thereof, or a pharmaceutically acceptable salt thereof, wherein:

R represents hydrogen or alkyl;

$R^1$ represents an alkyl group or a substituted or unsubstituted aryl group;

$R^2$ and $R^3$ each represent hydrogen, or $R^2$ and $R^3$ together represent a bond;

A represents a benzene ring having in total up to five substituents;

X represents oxygen, sulphur or a moiety $NR^4$ wherein $R^4$ represents hydrogen or alkyl; and n represents an integer in the range of from 2 to 6; a process for preparing such a compound, a composition containing such a compound and the use of the compound and composition in medicine.

12 Claims, No Drawings

NOVEL THIAZOLIDINEDIONES

This invention relates to certain novel urea and thiourea derivatives, to a process for preparing such compounds, to pharmaceutical compositions containing such compounds and to the use of such compounds and compositions in medicine.

European Patent Applications, Publication Nos. 0177353 and 0193256 disclose certain compounds as therapeutic agents against diabetes and hyperlipaemia.

It has surprisingly been discovered that certain novel urea and thiourea derivatives show good blood-glucose and blood-lipid lowering activity and are therefore of potential use in the treatment and/or prophylaxis of hyperglycaemia and hyperlipidaemia.

Accordingly, the present invention provides a compound of formula (I):

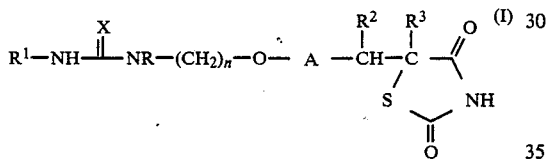

or a tautomeric form thereof, or a pharmaceutically acceptable salt thereof, wherein:

R represents hydrogen or alkyl;
$R^1$ represents an alkyl group or a substituted or unsubstituted aryl group;
$R^2$ and $R^3$ each represent hydrogen, or $R^2$ and $R^3$ together represent a bond;
A represents a benzene ring having in total up to five substituents;
X represents oxygen, sulphur or a moiety $NR^4$ wherein $R^4$ represents hydrogen or alkyl; and
n represents an integer in the range of from 2 to 6.

Suitably, R represents hydrogen or $C_{1-6}$ alkyl. Favourably R represents hydrogen. A favoured alkyl group for R is a methyl group.

Suitably, $R^1$ represents a substituted or unsubstituted phenyl group.

Favourably, $R^1$ represents a moiety of formula (a):

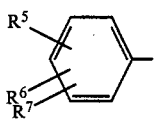

(a)

wherein $R^5$, $R^6$ and $R^7$ each independently represent hydrogen, halogen, substituted or unsubstituted alkyl or alkoxy.

Suitable substituents for the moiety A include halogen, substituted or unsubstituted alkyl or alkoxy.

Suitably $R^2$ and $R^3$ each represent hydrogen.
Suitably, A represents a moiety or formula (b):

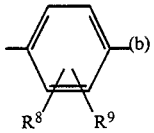

wherein $R^8$ and $R^9$ each independently represent hydrogen, halogen, substituted or unsubstituted alkyl or alkoxy.

Suitably, $R^8$ and $R^9$ each independently represent hydrogen, halogen, alkyl or alkoxy.

In one preferred aspect the present invention provides a class of compounds, which fall wholly within the scope of formula (I), of formula (II):

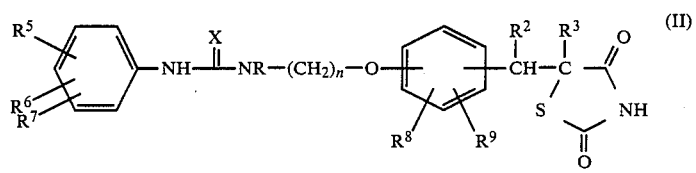

or a tautomeric form thereof, or a pharmaceutically acceptable salt thereof, wherein R, $R^2$, $R^3$, X and n are as defined in relation to formula (I); $R^5$, $R^6$ and $R^7$ are as defined in relation to moiety (a); and $R^8$ and $R^9$ are as defined in relation to moiety (b).

Suitably, X represents O or S.
Suitably, N represents 2, 3 or 4.
Preferably R represents hydrogen.
Preferably, $R^1$ represents an unsubstituted phenyl group, and thus, preferably, $R^5$, $R^6$ and $R^7$ each represent hydrogen.
Preferably, $R^8$ and $R^9$ each represent hydrogen.
Preferably, X represents 0.
Preferably, n represents 2.

As indicated above a compound of formula (I) may exist in one of several tautomeric forms, all of which are encompassed by the present invention.

The tautomeric forms of the compound of formula (I) include the following:

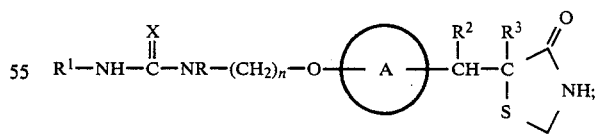

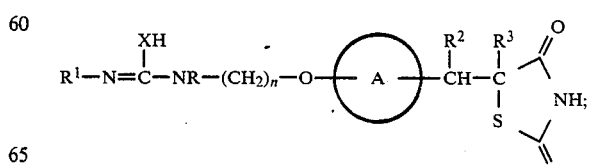

and, when R = H

-continued

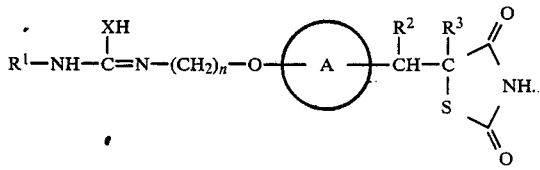

when used herein the term 'aryl' includes phenyl and naphthyl optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the term 'alkyl', or 'alkoxy' relates to groups having straight or branched carbon chains containing up to 12 carbon atoms.

Suitable alkyl groups are $C_{1-12}$ alkyl groups especially $C_{1-6}$ alkyl groups e.g. methyl, ethyl, n-propyl, iso-propyl, n-butyl, isobutyl or tert-butyl groups.

Suitable substitutents for any alkyl group include those indicated above in relation to the term "aryl".

A favoured substituted alkyl group is a trifluoromethyl group.

Suitable pharmaceutically acceptable salts include salts of the thiazolidinedione moiety, especially the nitrogen atom thereof, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

In a further aspect the present invention also provides a process for the preparation of a compound of formula (I), or a tautomeric form thereof, or a pharmaceutically acceptable salt thereof, which process comprises reacting a compound of formula (III):

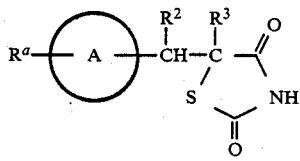 (III)

wherein $R^2$, $R^3$ and A are as defined in relation to formula (I), and $R^a$ is a moiety convertible to a moiety of formula

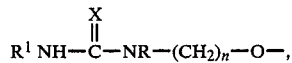

with an appropriate reagent capable of converting $R^a$ to the said moiety

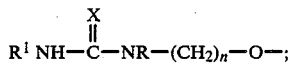

and thereafter, if required, carrying out one or more of the following optional steps:
(i) converting a compound of formula (I) to a further compound of formula (I); and
(ii) preparing a pharmaceutically acceptable salt of the compound of formula (I).

Suitably, $R^a$ represents $HRN—(CH_2)_n—O—$ wherein R and n are as defined in relation to formula (I).

Suitably, when $R^a$ is $HRN—(CH_2)n—O—$, an appropriate reagent capable of converting $R^a$ to

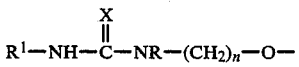

is a compound of formula (IV):

$$R^1—N=C=X^1 \qquad (IV)$$

wherein $R^1$ is as defined in relation to formula (I) and $X^1$ represents oxygen or sulphur.

The reaction between the compound of formula (III) and the appropriate reagent may be carried out under conditions suitable to the particular compound of formula (III) and the reagent chosen; thus for example the abovementioned reaction between a compound of formula (III) wherein $R^a$ represents $HRN—(CH_2)_n—O—$ and the compound of formula (IV), may be carried out in any suitable solvent, for example an aprotic solvent such as 1,2-dimethoxyethane, at a temperature in the range of between 0° and 100° C., for example 60° C.

A compound of formula (III) may be prepared from a compound of formula (V):

(V)

wherein A is as defined in relation to the compound of formula (I) and $R^b$ is a moiety $R^a$, or a moiety convertible to a moiety $R^a$; by reaction of the compound of formula (V) with 2,4-thiazolidinedione; and thereafter if required carrying out one or more of the following optional steps:
(i) reducing a compound of formula (III) wherein $R^2$ and $R^3$ together represent a bond, into a compound of formula (III) wherein $R^2$ and $R^3$ each represent hydrogen; and
(ii) converting a moiety $R^b$ to a moiety $R^a$.

The reaction between the compound of formula (V) and 2,4-thiazolidinedione will of course be carried out under conditions suitable to the nature of the compound of formula (V), but in general the reaction may be carried out in a solvent such as toluene, suitably at an elevated temperature such as the reflux temperature of the solvent and preferably in the presence of a suitable catalyst such as piperidinium benzoate. Favourably, in the reaction between the compound of formula (V) and 2,4-thiazolidinedione, the water produced in the reaction is removed from the reaction mixture, for example by means of a Dean and Stark apparatus.

Suitably, $R^b$ is a moiety convertible to a moiety $R^a$, for example $R^b$ may represent $HO(CH_2)_n-O-$.

The moiety $R^b$ may be converted to the moiety $R^a$ by any suitable means, for example when $R^b$ represents $HO(CH_2)_n-O-$ and $R^a$ represents $HRN(CH_2)_n-O-$, the appropriate conversion may be carried out as shown in the following reaction scheme:

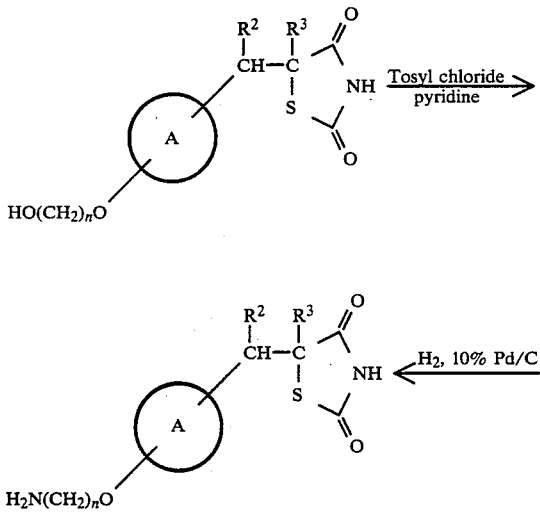

The compounds of formula (V) are known compounds or compounds prepared by methods analogous to those used to prepare known compounds, for example the compounds of formula (V) wherein $R^b$ is $HO(CH_2)_n-O-$ may be prepared using the methods described in Journal of the American Chemical Society 1951, 73, 906-912.

A compound of formula (I), or a pharmaceutically acceptable salt thereof, may also be prepared by reacting a compound of formula (VI):

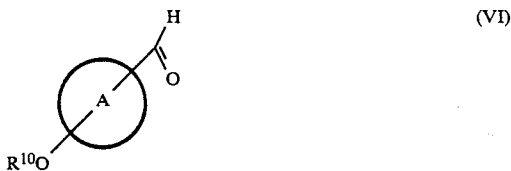

wherein A is as defined in relation to formula (I) and $R^{10}$ is a moiety

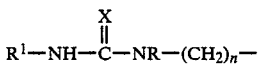

or a protected form thereof, with 2,4-thiazolidinedione; and thereafter if required carrying out one or more of the following optional steps:
(i) converting a compound of formula (I) into a further compound of formula (I); and
(ii) preparing a pharmaceutically acceptable acid addition salt of a compound of formula (I).
Preferably $R^{10}$ represents

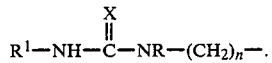

The reaction between a compound of formula (VI) and 2,4-thiazolidinedione may suitably be carried out under analogous conditions to those used in the reaction between a compound of formula (V) and 2,4-thiazolidinedione.

A compound of formula (VI) may be prepared by reacting a compound of formula (VII):

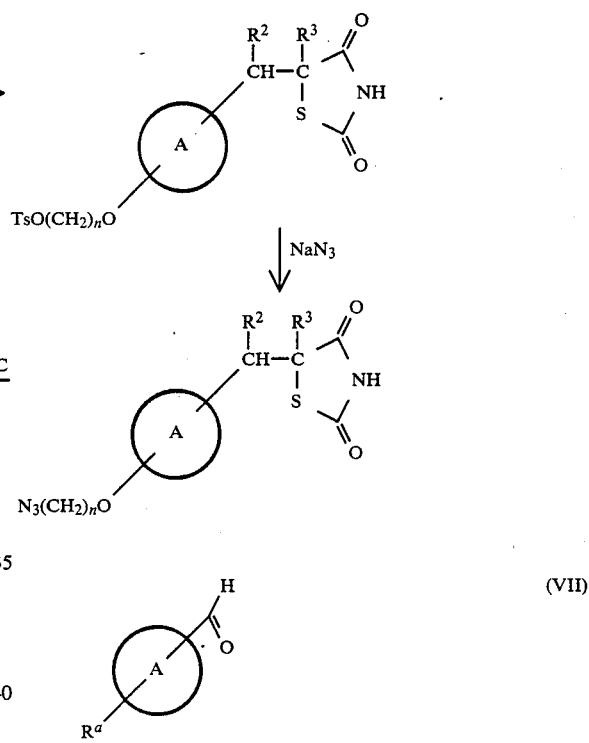

wherein A is as defined in relation to formula (I) and $R^a$ is as defined in relation to formula (III), with an appropriate reagent capable of converting $R^a$ to the moiety

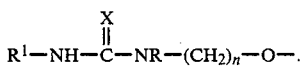

Suitable values for $R^a$ include those described above in relation to the compound of formula (III).

Suitable reaction conditions for the reaction of the compound of formula (VII) and the appropriate reagent may include those described above in relation to the preparation of compound (III) with the said appropriate reagent.

A particularly favoured form of the process for preparing a compound of formula (VI) from a compound of formula (VII) is that wherein $R^a$ represents a leaving group, preferably a fluorine atom, and the appropriate reagent is a compound of formula (VIII):

$R^{10}-OH$         (VIII)

wherein $R^{10}$ is as defined in relation to formula (VI).

The reaction between the compounds of formulae (VII) and (VIII) may be carried out under any suitable conditions, for example in a solvent such as dimethylsulphoxide at an elevated temperature for example in the range of between 100° to 150° C.

The compounds of formula (VII) are either known compounds or they may be prepared using methods analogous to those used to prepare known compounds, for example 4-fluorobenzaldehyde is a known commercially available compound.

A compound of formula (VIII) may be prepared by reacting a compound of the hereinabove defined formula (IV), with a compound of formula (IX):

$$HRN-(CH_2)_n-OH \qquad (IX)$$

wherein R and n are as defined in relation to formula (I).

The reaction between the compounds of formula (IV) and (IX) may be carried out under any suitable conditions, for example in a solvent such as tetrahydrofuran at a temperature in the range of between 0° to 30° C.

The abovementioned conversion of a compound of formula (I) into a further compound of formula (I) includes the following conversions:

(a) reducing a compound of formula (I) wherein $R^2$ and $R^3$ together represent a bond, to a compound of formula (i) wherein $R^2$ and $R^3$ each represent hydrogen;

(b) converting a compound of formula (I) wherein X represents O or S, to a acompound of formula (I) wherein X represents a moiety $NR^4$ as defined above; and (c) converting a compound of formula (I) wherein $R^4$ represents hydrogen into a compound of formula (I) wherein $R^4$ represents an alkyl group.

The converison of a compound of formula (I) to a further compound of formula (I) may be carried out by using any suitable method:

A suitable reduction method for the abovementioned conversion (a) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

In the abovementioned conversion (b), the compound of formula (I) wherein X represents O or S may be converted into a further compound of formula (I) wherein X represents a moiety $NR^4$, by for example treating the appropriate compound of formula (I) with an alkylating agent such as methyl iodide and thereafter with an appropriate amine $R^4NH_2$.

In the abovementioned conversion (c), the compound of formula (I) wherein $R^4$ represents hydrogen may be converted into a further compound of formula (I) wherein $R^4$ represents alkyl by treating the appropriate compound of formula (I) with a suitable alkylating agent, for example an alkyl halide, preferably an alkyl iodide.

The abovementioned reduction of a compound of formula (III) wherein $R^2$ and $R^3$ together represent a bond to a compound of formula (III) wherein $R^2$ and $R^3$ each represent hydrogen, may be carried out under analogous conditions to those referred to above in conversion (i) of the compound of formula (I).

The present invention also provides a compound of formula (I), or a pharmaceutically acceptable salt thereof, for use as an active therapeutic substance.

Thus the present invention provides a compound of formula (I), or a tautomeric form thereof, or a pharmaceutically acceptable salt thereof, for use in the treatment of and/or prophylaxis of hyperglycaemia.

In a further aspect the present invention also provides a compound of formula (I), or a tautomeric form thereof, or a pharmaceutically acceptable salt thereof, for use in the treatment and/or prophylaxis of hyperlipidaemia.

A compound of the general formula (I), or a tautomeric form thereof, or a pharmaceutically acceptable salt thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic amount of a compound of the general formula (I), or a tautomeric form thereof, or a pharmaceutically acceptable salt thereof, to a hyperglycaemic human or non-human mammal in need thereof.

The present invention further provides a method for the treatment of hyperlipidaemia in a human or non-human mammal, which comprises administering an effective, non-toxic amount of a compound of the general formula (I), or a tautomeric form thereof, or a pharmaceutically acceptable salt thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and or prophylaxis of hyperlipidaemic human, the compound of the general formula (I), or a tautomeric form thereof, or a pharmaceutically acceptable salt thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The present invention also provides the use of a compound of formula (I), or a tautomeric form thereof, or a pharmaceutically acceptable salt thereof, for the manufacture of a medicament for the treatment and/or prophylaxis of hyperglycaemia.

The present invention further provides the use of a compound of formula (I) or a tautomeric form thereof, or a pharmaceutically acceptable salt thereof, for the manufacture of a medicament for the treatment and/or prophylaxis of hyperlipidaemia.

The following Examples illustrate the invention but do not limit it in any way.

EXAMPLE 1

5-{4-[2-(N-(N$^1$-Phenylthioureido)Ethoxy)]Benzyl}-2,4-Thiazolidinedione

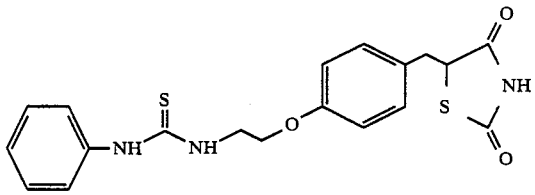

To a solution of 5-[4-(2-Aminoethoxy)Benzyl]-2,4-Thiazolidinedione (1.00 g) in dry 1,2-Dimethoxyethane (50 ml) was added a solution of phenylisothiocyanate (0.77 g) in 1,2-Dimethoxyethane (10 ml), dropwise, at room temperature. The mixture was warmed to 60° C. to effect complete solution and stirred at this temperature for 30 minutes. The solvent was evaporated and the title compound (m.p. 132°-3° C., Diethylether-Ethyl Acetate) was obtained pure after chromatography on silica-gel in 5% Methanol-Dichloromethane followed by recrystallisation.

$^1$H NMR δ(DMSO-d$_6$): 3.0-3.4 (2H, complex); 3.75-3.95 (2H, complex); 4.1-4.2 (2H, complex); 4.85 (1H, complex); 6.9-7.5 (9H, complex); 7.8-8.0 (1H, broad s, exchanges with D$_2$O); 9.7 (1H, s, exchanges with D$_2$O); 12.0 (1H, broad s, exchanges with D$_2$O).

EXAMPLE 2

5-{4-[2-(N-(N$^1$-Phenylureido)Ethoxy)]Benzyl}-2,4-Thiazolidinedione

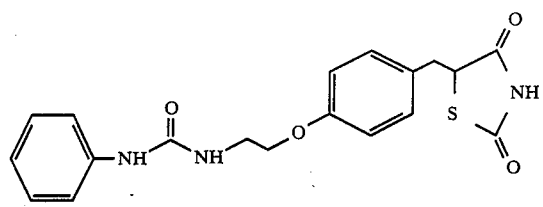

5-{4-[2-(N-(N$^1$-Phenylureido)Ethoxy)]Benzylidene}2,4-Thiazolidinedione (3.2 g) in dry 1,4-Dioxan (100 ml) was reduced under hydrogen in the presence of 10% palladium on charcoal (5g) until hydrogen uptake ceased. The solution was filtered through diatomaceous earth, the filter pad washed exhaustively with Dioxan and the combined filtrates were evaporated to dryness under vacuum. The title compound (m.p. 178°-9° C.) was obtained pure after chromatography on silica-gel in 2% Methanol-Dichloromethane.

$^1$H NMR δ(DMSO-d$_6$): 3.0-3.3 (2H, complex); 3.4-3.5 (2H, complex); 3.95-4.05 (2H, complex); 4.85 (1H, complex); 6.4 (1H, t, exchanges with D$_2$O); 6.8-7.5 (9H, complex); 8.55 (1H, s, exchanges with D$_2$O); 12.0 (1H, Broad s, exchanges with D$_2$O).

EXAMPLE 3

5-[4-[2-(N-Methyl-N'-phenylureido)ethoxy]benzyl]2,4-thiazolidinedione

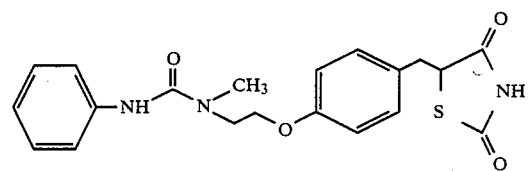

The title compound (mp 88°-90° C., methanol) was obtained from 5-[4-[2-(N-methyl-(N'-phenylureido)ethoxy]benzylidene]-2,4-thiazolidinedione by an analogous procedure to that described in Example 1.

$^1$H NMR δ(DMSO-d$_6$+D$_2$O): 3.0-3.4 (2H, complex); 3.05 (3H, s); 3.65 (2H, t); 4.2 (2H, t); 4.85 (1H, complex); 6.9-7.5 (9H, complex), 8.3 (1H, s, exchanges very slowly with D$_2$O).

EXAMPLE 4

5-[4-[2-(N-(N'-Phenylureido)ethoxy)]benzylidene]2,4-thiazolidinedione

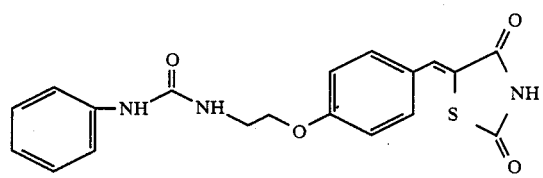

4-[2-(N-(N'-Phenylureido)ethoxy)]benzaldehyde (3.7 g) and 2,4-thiazolidinedione (1.53 g) were mixed in dry toluene (100 ml) in the presence of a catalytic quantity of piperidinium acetate. The mixture was boiled under reflux in a Dean and Stark apparatus until no more water was evolved. The solution was cooled and the title compound obtained pure by filtration.

¹H NMR δ(DMSO-d₆+D₂O): 3.4–3.5 (2H, complex); 3.9–4.05 (2H, complex); 6.8–7.7 (10H, complex).

EXAMPLE 5

5-[4-[2-(N-Methyl-(N'-phenylureido)ethoxy)]-benzylidene]-2,4-thiazolidinedione

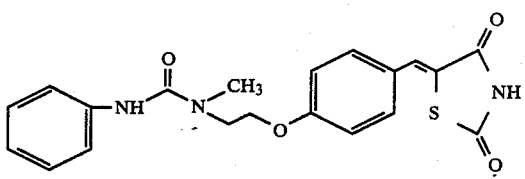

The title compound (mp 219°–21° C.) was obtained from 4-[2-(N-methyl-(N'-phenylureido)ethoxy)]benzaldehyde and 2,4-thiazolidinedione by an analogous procedure to that described in Example 4.

¹H NMR δ(DMSO-d₆+D₂O): 3.10 (3H, s); 3.65 (2H, t); 4.3 (2H, t); 6.9–7.8 (10H complex).

EXAMPLE X1

5-[4-(2-Aminoethoxy)Benzyl]-2,4-Thiazolidine-dione

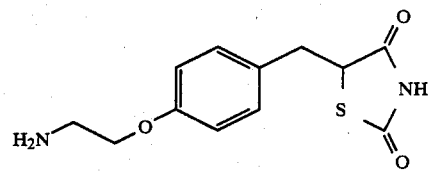

A solution of 5-[4-(2-Azidoethoxy)Benzyl]2,4-Thiazolidinedione (5 g) in Methanol (100 ml) was reduced under hydrogen at ambient temperature and pressure in the presence of 10% palladium on charcoal (5 g) for 18 hours. The mixture was filtered through diatomaceous earth and the filter pad was washed exhaustively with Methanol. The combined filtrates was evaporated to dryness under reduced pressure and the title compound (m.p. 175°–6° C.) was obtained as a dihydrate following crystallisation from methanol.

¹H NMR δ(DMSO d₆+D₂O): 2.75–2.8 (1H, complex); 3.15–3.2 (2H, complex); 3.25–3.3 (1H, complex), 4.1 (2H, t); 4.3 (1H, complex); 6.85 (2H, d); 7.15 (7.2; 2H, d).

EXAMPLE X2

5-[4-(2-Azidoethoxy)Benzyl]-2,4-Thiazolidinedione

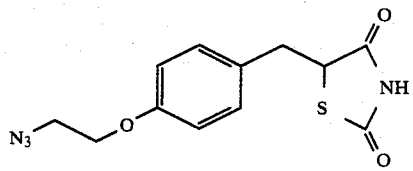

To a solution of 5-[4-(2-Tosyloxyethoxy)Benzyl]-2,4-Thiazolidinedione (12.5 g) in dry Dimethylsulphoxide (80 ml) was added sodium azide (2 g) in one portion. The mixture was stirred at ambient temperature for 18 hours and the resulting solution added to water (250 ml). The aqueous solution was extracted with dichloromethane (2×300 ml) and the combined organic phases were washed with water (3×300 ml), dried (MgSO₄), filtered and evaporated to give the title compound as an oil which was used in the next stage without further purification.

¹H NMR δ(CDCl₃):
2.9–4.0 (2H, complex); 3.5 (2H, t); 4.1 (2H, t) 4.3–4.6 (1H. complex); 6.8 (2H, d); 7.1 (2H, d) 9.0–9.4 (1H, broad s, exchanges with D₂O).

EXAMPLE X3

5-[4-(2-Tosyloxyethoxy)Benzyl]-2,4-Thiazolidinedione

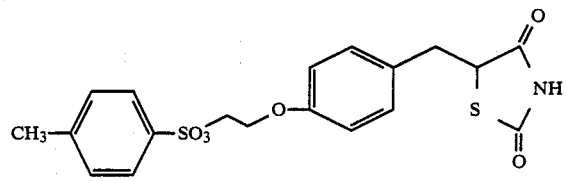

A solution of 5-[4-(2-Hydroxyethoxy)Benzyl]-2,4-Thiazolidinedione (5.34 g) in pyridine (50 ml) was cooled to below 5° C. Toluenesulphonyl chloride (3.82 g) was added portionwise to the stirred solution and the mixture was allowed to stand overnight at below 5° C. The solution was poured into water (200 ml) and extracted with dichloromethane (2×200 ml). The organic extracts washed with 5% hydrochloric acid solution and water, dried (MgSO₄), filtered and evaporated under reduced pressure to give an oil which was used without further purification.

¹H NMR δ(CDCl₃): 2.45 (3H, s); 2.9–4.5 (6H, complex); 4.6–5.0 (1H, complex); 6.6–8.0 (9H, complex, 1H exchanges with D₂O).

EXAMPLE X4

5-[4-(2-Hydroxyethoxy)Benzyl]-2,4-Thizaolidinedione

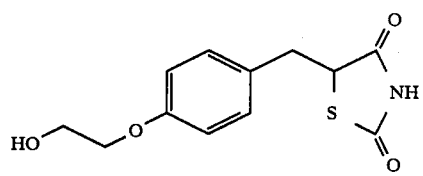

2,4-Thiazolidinedione (46 g) and 4-(2-Hydroxyethoxy)Benzaldehyde (65 g) were mixed in toluene (400 ml) containing acetic acid (1.0 ml) and piperidine (1.0 ml) in an apparatus incorporating a water-trap. The mixture was boiled under reflux with vigorous stirring for 30 minutes, during which time the theoretical quantity of water was obtained and 5-[4-(2-Hydroxyethoxy)Benzylidene]-2,4-Thiazolidinedione started to crystallise. The solution was cooled and the Banzylidene compound (MP 194°–196° C.) collected by filtration. This product was suspended in Methanol (2 L.) and treated portionwise with Magnesium turnings (2 g). When the vigorous reaction started a cooling bath was applied and the rest of the magnesium (78 g) was added portionwise with stirring. The mixture was stirred overnight at ambient temperature and the solvent was then evaporated. 5% Hydrochloric acid soln. (100 ml), water (500 ml) and Methanol (50 ml) were added. When gas evolution ceased the mixture was extracted with dichloromethane, the organic phase dried (MgSO₄), filtered and evaporated under reduced pressure. The title compound was obtained pure by crystallisation from aqueous methanol (M.P. 137°-9° C).

$^1$H NMR δ(DMSO-d$_6$): 2.9-4.2 (2H, complex); 3.7 (2H, t); 3.9 (2H, t); 4.8 (1H, complex); 4.3-5.2 (1H. broad s, exchanges with D$_2$O); 6.85 (2H, d) 7.15 (2H, d); 11.5-12.5 (1H, Broad s, exchanges with D$_2$O).

EXAMPLE X5

4-[2-(N-Methyl-(N'-phenylureido)ethoxy)]benzaldehyde

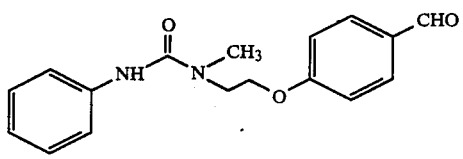

N'-(2-Hydoxyethyl)-N'-methyl-N-phenyl-urea (8.7 g) was dissolved in dry dimethylsulphoxide (70 ml), 4-fluorobenzaldehyde (12.4 g) and potassium carbonate (15 g) were added and the mixture was stirred at 120° C. for 6 hours. After cooling the mixture was added to iced water, the aqueous solution was extracted with ethyl acetate (2×500 ml), the combined organics washed with brine (2×700 ml), dried (MgSO$_4$), filtered and evaporated under reduced pressure. The title compound (mp 107°-8° C.) was obtained pure by chromatography on silica-gel in 2% methanol-dichloromethane.

$^1$H NMR δ(DMSO-d$_6$): 3.05 (3H, s); 3.7 (2H, t); 4.2 (2H, t); 6.8-7.8 (9H, complex); 8.3 (1H, board s, exchanges slowly with D$_2$O), 9.9 (1H, s).

EXAMPLE X6

4-[2-(N-(N'-Phenylureido)ethoxy)]benzyaldehyde

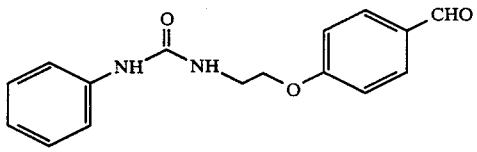

The title compound was obtained as an oil from N-hydroxyethyl-N'-phenylurea by an analogous procedure to that described in Example X5

$^1$H NMR δ(DMSO-d$_6$): 3.6 (2H, t); 4.2 (2H, t); 6.4 (1H, t, exchanges with D$_2$O); 6.8-8.0; (9H; complex); 8.5 (1H, s, exchanges slowly with D$_2$O); 9.9 (1H, s).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (Mmol kg$^{-1}$ of DIET) | % REDUCTION IN AREA UNDER BLOOD GLUCOSE CURVE |
|---|---|---|
| 1 | 1 | 43 |
| 2 | 1 | 58 |

Toxicology

No toxicological effects were indicated for any of the compounds of the invention in any of the abovementioned tests.

We claim:

1. A compound of formula (I):

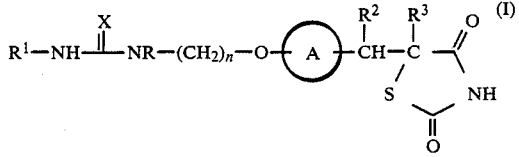

or a tautomeric form thereof, or a pharmaceutically acceptable salt thereof, wherein:

R represents hydrogen or C$_{1-12}$ alkyl;

R$^1$ represents an C$_{1-12}$ alkyl group or a substituted or unsubstituted phenyl or naphthyl group;

R$^2$ and R$^3$ each represent hydrogen, or R$^2$ and R$^3$ together represent a bond;

A represents a benzene ring having in total up to three substituents;

X represents oxygen, sulphur or a moiety NR$^4$ wherein R$^4$ represents hydrogen or C$_{1-12}$ alkyl; and n represents an integer in the range of from 2 to 6;

wherein optional substituents for any phenyl or naphthyl group includes up to five groups selected from halogen, alkyl, phenyl, alkoxy, haloalkyl, hydroxy, amino, nitro, carboxy, alkoxycarbonyl, alkoxycarbonylalkyl, alkylcarbonyloxy or alkylcarbonyl groups, wherein the alkyl or alkoxy groups have 1 to 12 carbon atoms.

2. A compound according to claim 1, wherein R$^1$ represents a moiety of formula (a):

wherein R$^5$, R$^6$ and R$^7$ each independently represent hydrogen, halogen, substituted or unsubstituted alkyl or alkoxy.

3. A compound according to claim 1, wherein A represents a moiety or formula (b):

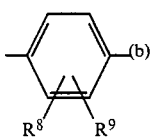

wherein $R^8$ and $R^9$ each independently represent hydrogen, halogen, substituted or unsubstituted alkyl or alkoxy.

4. A compound according to claim 1 of formula (II):

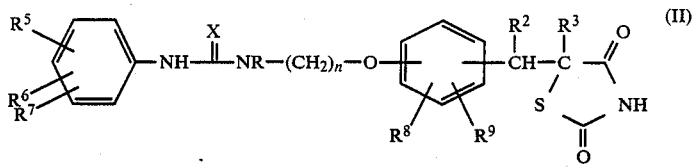

or a tautomeric form thereof, or a pharmaceutically acceptable salt thereof, wherein R, $R^2$, $R^3$, X and n are as defined in relation to formula (I) of claim 1; $R^5$, $R^6$ and $R^7$ each independently represent hydrogen, halogen, substituted or unsubstituted alkyl or alkoxy and $R^8$ and $R^9$ each independently represent hydrogen, halogen, substituted or unsubstituted alkyl or alkoxy.

5. A compound according to claim 2, wherein $R^5$, $R^6$ and $R^7$ each represents hydrogen.

6. A compound according to claim 3, wherein $R_8$ and $R^9$ each represent hydrogen.

7. A compound according to claim 1, wherein X represents O.

8. A compound according to claim 1, wherein n represents 2.

9. 5-[4-[2-(N-($N^1$-Phenylthioureido)ethoxy)]benzyl]2,4-thiazolidinedione, or a tautomeric form thereo, or a pharmaceutically acceptable salt thereof.

10. 5-[4-[2-(N-($N^1$-Phenylureido)ethoxy)]benzyl]2,4-thiazolidinedione, or a tautomeric form thereof, or a pharmaceutically acceptable salt thereof.

11. A pharmaceutical composition comprising a non-toxic, pharmaceutically effective amount of a compound of the general formula (I), or a tautomeric form thereof, or a pharmaceutically acceptable salt thereof, and a pharmaceutically acceptable carrier therefor.

12. A method for the treatment and/or prophylaxis of hyperglycaemia or hyperlipidaemia in a human or non-human mammal which comprises administering an effective, non-toxic, amount of a compound of the general formula (I), or a tautomeric form thereof, or a pharmaceutically acceptable salt thereof, to a hyperglycaemic human or non-human mammal in need thereof.

* * * * *